United States Patent [19]

Alink

[11] 4,146,714

[45] Mar. 27, 1979

[54] PREPARATION OF Δ-2 TETRAHYDROPYRIMIDINES

[75] Inventor: Bernardus A. O. Alink, St. Louis, Mo.

[73] Assignee: Petrolite Corporation, St. Louis, Mo.

[21] Appl. No.: 802,347

[22] Filed: Jun. 1, 1977

Related U.S. Application Data

[63] Continuation-in-part of Ser. No. 384,439, Aug. 1, 1973, abandoned, which is a continuation-in-part of Ser. No. 292,494, Sep. 27, 1972, Pat. No. 4,085,104.

[51] Int. Cl.$^2$ ............................................. C07D 239/02
[52] U.S. Cl. ..................................... 544/242; 544/333
[58] Field of Search ................... 260/251 R; 544/333, 544/242

[56] References Cited

U.S. PATENT DOCUMENTS

| | | | |
|---|---|---|---|
| 3,904,625 | 9/1975 | Alink | 260/251 R |
| 3,943,134 | 3/1976 | Kajiyama et al. | 260/251 R |
| 4,001,232 | 1/1977 | Groegler et al. | 260/251 R |

Primary Examiner—Nicholas S. Rizzo
Attorney, Agent, or Firm—Sidney B. Ring; Hyman F. Glass

[57] ABSTRACT

A process of converting 2,3,4,5-tetrahydropyrimidines (Δ-1) having at least one hydrogen in the 2-position to 3,4,5,6-tetrahydropyrimidines (Δ-2), which comprises hydrogenating and dehydrogenating said Δ-1 tetrahydropyrimidines. Such hydrogenating and dehydrogenating may be done in either two sequential steps or in one step.

Said Δ-1 tetrahydropyrimidines can also be converted to Δ-2 tetrahydropyrimidines by heating in the essential absence of a solvent, and preferably under basic conditions.

In addition, corresponding hexahydropyrimidines can be converted to corresponding Δ-2 tetrahydropyrimidines by dehydrogenation.

This invention also relates to the use of Δ-2 tetrahydropyrimidines, particularly as corrosion inhibitors.

9 Claims, No Drawings

PREPARATION OF Δ-2 TETRAHYDROPYRIMIDINES

This application is a Continuation-in-Part of my Application Ser. No. 384,439 filed Aug. 1, 1973 now abandoned which is a Continuation-in-Part of my Application Ser. No. 292,494 filed Sept. 27, 1972 now Pat. No. 4,085,104.

In Ser. No. 292,494 filed on Sept. 27, 1972 there is described and claimed substituted 2,3,4,5-tetrahydropyrimidines (THP)

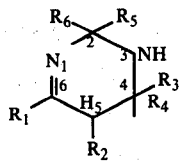

which are prepared by the following reactions:
1. The reaction of a carbonyl compound (ketone or aldehyde) with ($NH_3$ or $NH_4OH$) and a sulfurcontaining catalyst.
2. The reaction of an α, β-unsaturated ketone and a carbonyl compound and $NH_3$ (or $NH_4OH$) without a catalyst.
3. Reaction of an α, β-unsaturated ketone, a 1-aminoalcohol and $NH_3$ (or $NH_4OH$) without a catalyst.

In the above formula, $R_1$, $R_2$, $R_3$, $R_4$, $R_5$ and $R_6$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc. for example having about 1–25 or more carbons such as from about 1–18 carbons, but preferably about 1–12 carbons. The term "alkyl" also includes isomers of the straight chain where branching occurs.

Cycloalkyl includes cyclopentyl, cyclohexyl, etc. and derivatives thereof such as alkyl cyclohexyl, dialkylcyclohexyl, etc.

Aryl, alkaryl and aralkyl include phenyl, alkylphenyl, polyalkylphenyl, chlorophenyl, alkoxyphenyl, naphthyl, alkylnaphthyl, etc., benzyl, substituted benzyl, etc.

The joining of the R groups into a ring structure includes those structures derived from reactants of the general formula

such as cyclohexanone, cyclopentanone, substituted derivatives thereof such as alkyl-cyclohexanone, dialkyl-cyclohexanone.

I have discovered that the 2,3,4,5-tetrahydropyrimidines (i.e., Δ-1 THP) of S.N. 292,494 containing at least 1 hydrogen in the 6-position can be converted to the corresponding 3,4,5,6-tetrahydropyrimidines (i.e., Δ-2 THP) by
1. Hydrogenation - dehydrogenation in sequential steps.
2. A single hydrogenation-dehydrogenation reaction.
3. Heating under conditions whereby hydrogen undergoes a 1-3 prototopic shift (i.e., from the 2-position to the 6-position without conventional hydrogenation-dehydrogenation) so as to shift the double bond from the 1-6 position to the 1-2 position.

Δ-1 THP means having a double bond between the 6 carbon and the 1 nitrogen.

Δ-2 THP means having a double bond between the 1 nitrogen and the 2 carbon.

Thus the preparation of substituted 3,4,5,6-tetrahydropyrimidines (Δ-2 THP's), from substituted 2,3,4,5-tetrahydropyrimidines (Δ-1 THP's)

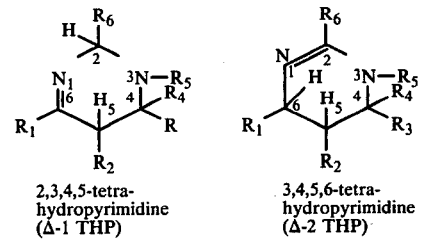

2,3,4,5-tetra-hydropyrimidine (Δ-1 THP)     3,4,5,6-tetra-hydropyrimidine (Δ-2 THP)

is effected by the following methods.

Method 1. By reduction of a Δ-1 THP to produce a hexahydropyrimidine (HHP) followed by catalytic dehydrogenation of the HHP to produce a Δ-2 THP according to the following equation:

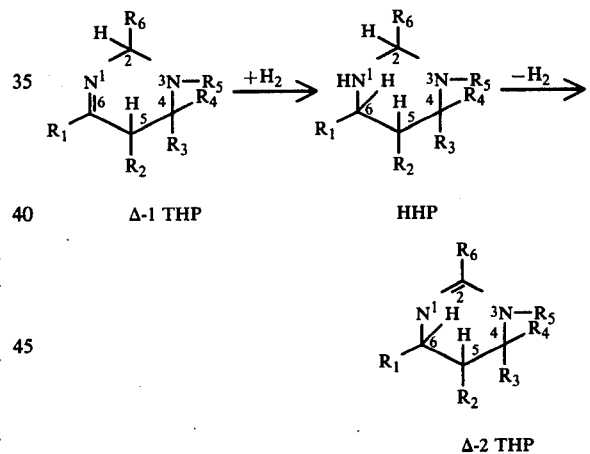

Δ-1 THP     HHP

Δ-2 THP

The first step, formation of a HHP from a Δ1-THP ca be performed by any suitable reducing agent such as sodium ethanol, sodiumboron hydride, $LiAlH_4$, sodium bisolfite, magnesium/methanol, a hydrogenation catalyst such as platinum, palladium, cobalt, nickel, etc. The conversion of the HHP to Δ-2 THP is carried out by a process which requires a catalyst with dehydrogenation properties. Suitable catalysts for this reaction are platinum, palladium, nickel, cobalt, copper chromite, chromia. Temperatures are from ambient to 300° C. depending on the HHP and catalyst used. Solvents can be used but are not necessary. Examples 1–17 illustrate this method.

Method 2. This method is the same as method 1, except that less than 1 equivalent of hydrogen is used. Without isolating the HHP, the Δ-1 THP is converted to the Δ-2 THP. The reaction is a hydrogenation/dehydrogenation process using catalysts capable of hydrogenating and dehydrogenating such as platinum, palladium, nickel, cobalt, copper chromite, chromia, etc. No hydrogen is consumed or produced in the overall process. Temperatures and solvents as in method 1. Examples 18-29 illustrate this method.

Method 3. In certain instances Δ-1 THP's can be converted to Δ-2 THP's by simply heating Δ-1 THP's without solvent or in the presence of a base (NaOH, KOH, etc.). The reaction involves a 1.3 prototopic shift. That is the hydrogen in the 2-position is transferred to the 6-position and the double bond shifts from the 1-6 position to the 1-2 position. This process is particularly effective where $R_6$ is an aromatic group, such as phenyl, furyl, pyridyl, etc. Examples 30-35 illustrate this method.

The following examples are presented by way of illustration and not of limitation.

EXAMPLE 1

4,4,6-trimethyl - 3,4,5,6-tetrahydropyrimidine

A sample of 392 grams of mesityloxide and 800 cc of 28% aqueous ammoniumhhydroxide were stirred in a closed reaction vessel for 3 hrs. The mixture was allowed to stand for 15 hrs. To the solution was added over a ½ hr. period 300 cc. of a 37% solution of formaldehyde in water. After the addition was completed, the mixture was stirred for 3 hrs. Distillation of the product yielded 419 grams of 4,4,6-trimethyl-2,3,4,5-tetrahydropyrimidine as a colorless liquid $b_{15}$ 62°–65° C.

To a sample of 126 grams of 4,4,6-trimethyl-2,3,4,5-tetrahydropyrimidine in 300 cc. of methanol was added with stirring and cooling over a 2 hr. period 20.8 grams of sodium boronhydride. The mixture was allowed to stand for 17 hrs. The reaction mixture was extracted with chloroform and the chloroform removed under diminished pressure. The remaining product was distilled and the fraction $b_{25}$ 76.5°–77° C. was collected as 108 grams of 4,4,6-trimethyl hexahydropyrimidine. Anal. Calc.ed for $C_7H_{16}N_2$ : N, 21.85. Found: N, 21.6 Nuclear magnetic resonance spectrum, solvent CDCl$_3$, δ in ppm; 3.82 s, 2H; 2.87 m, 1H; 1.42 & 1.65, 2d's, 2H; 1.02 d, 3H; 1.08 & 1.13 2s's, 6H; 1.67 s, 2H exchangeable with D$_2$O. A sample of 12.8 grams of 4,4,6-trimethylhexahydropyrimidine and 0.5 grams of 60% nickel catalyst on kieselguhr was heated for 8 hrs. at 185°–187° C. During this time the theoretial amount of hydrogen gas was evolved.

The product was distilled under diminished pressure to yield 10.0 grams of 4,4,6-trimethyl-3,4,5,6-tetrahydropyrimidine $b_{0.6}$ 78°–82° C. solidified during distillation. Infrared spectrum, 3.16μ, N-H; 6.19μ, C=N. Nuclear magnetic resonance spectrum, solvent CCl$_4$, 6.87 s, 1H; 3.25 m, 1H; 1.61 d of d's, 2H; 1.12 d, 3H; 1.12 & 1.07 2 s's, 6H; 7.75, s, 1H. exchangeable with D$_2$O.

Anal. Calc.ed for $C_7H_{14}N_2$; N, 22.2 Found; N, 21.9

EXAMPLE 2

4,4,6-trimethyl-3,4,5,6-tetrahydropyrimidine

Heating a mixture of 12.8 g. of 4,4,6-trimethylhexahydropyrimidine and 0.5 g. of platinum on alumina catalyst at 185°–190° C. for 6½ hrs. produced 4,4,6-trimethyl-3,4,5,6-tetrahydropyrimidine in 90% yield.

EXAMPLE 3

4,4,6-trimethyl-3,4,5,6-tetrahydropyrimidine

Heating a mixture of 12.6 g. of 4,4,6-trimethyl hexahydropyrimidine and 0.5 g. of palladium on alumina catalyst at 185°–190° C. for 24 hrs. produced 4,4,6-trimethyl-3,4,5,6-tetrahydropyrimidine in 88% yield.

EXAMPLE 4

4,4,6-trimethyl-3,4,5,6-tetrahydropyrimidine

Heating a mixture of 12.6 g of 4,4,6-trimethyl hexahydropyrimidine and 0.5 g. of cobalt oxide on kieselguhr for 9 hrs. at 185°–190° C. yielded 10% of 4,4,6-trimethyl-3,4,5,6-tetrahydropyrimidine.

In Table I the production of several substituted 3,4,5,6-tetrahydropyrimidines from the corresponding hexahydropyrimidines is shown. The products were prepared in the manner described in example 1.

Table I

| Ex. No. | $R_1$ | $R_2$ | $R_3$ | $R_4$ | $R_5$ | $R_6$ |
|---|---|---|---|---|---|---|
| 5 | CH$_3$ | H | CH$_3$ | CH$_3$ | H | CH$_3$ |
| 6 | CH$_3$ | H | CH$_3$ | CH$_3$ | H | C$_2$H$_5$ |
| 7 | CH$_3$ | H | CH$_3$ | CH$_3$ | H | i-C$_3$H$_7$ |
| 8 | CH$_3$ | H | CH$_3$ | CH$_3$ | H | n-C$_3$H$_7$ |
| 9 | CH$_3$ | H | CH$_3$ | CH$_3$ | H | CH(C$_2$H$_5$)$_2$ |
| 10 | CH$_3$ | H | CH$_3$ | CH$_3$ | H | n-C$_6$H$_{13}$ |
| 11 | CH$_3$ | H | CH$_3$ | CH$_3$ | CH$_3$ | CH$_3$ |
| 12 | H | CH$_3$ | C$_2$H$_5$ | H | H | C$_2$H$_5$ |
| 13 | H | C$_2$H$_5$ | n-C$_3$H$_7$ | H | H | n-C$_3$H$_7$ |
| 14 | H | C$_2$H$_5$ | n-C$_3$H$_7$ | H | H | c-C$_3$H$_7$ |
| 15 | H | n-C$_5$H$_{11}$ | n-C$_6$H$_{13}$ | H | H | n-C$_6$H$_{13}$ |
| 16 | CH$_3$ | H | CH$_3$ | CH$_3$ | H | Phenyl |
| 17 | CH$_3$ | H | CH$_3$ | CH$_3$ | H | Furyl |

EXAMPLE 18

4,4,6-trimethyl-3,4,5,6-tetrahydropyrimidine

A sample of 12 g. of 4,4,6-trimethyl-2,3,4,5-tetrahydropyrimidine and 1.0 g. of W-2 Raney nickel were heated under a hydrogen atmosphere at 178° C. for 18 hrs. to yield 4,4,6-trimethyl-3,4,5,6-tetrahydropyrimidine identical to the product described in example 1.

EXAMPLE 19

As in example 18, instead of W-2 Raney nickel a platinum on alumina catalyst was used.

EXAMPLE 20

As example 18, instead of W-2 Raney nickel a palladium on alumina catalyst was used.

The substituted 3,4,5,6-tetrahydropyrimidine prepared as in the manner of example 18 by catalytic conversion of the corresponding 2,3,4,5-tetrahydropyrimidines are summarized in Table II.

Table II

| Ex. No. | $R_1$ | $R_2$ | $R_3$ | $R_4$ | $R_5$ | $R_6$ |
|---|---|---|---|---|---|---|
| 21 | $CH_3$ | H | $CH_3$ | $CH_3$ | H | $CH_3$ |
| 22 | $CH_3$ | H | $CH_3$ | $CH_3$ | H | $C_2H_5$ |
| 23 | $CH_3$ | H | $CH_3$ | $CH_3$ | H | $i\text{-}C_3H_7$ |
| 24 | $CH_3$ | H | $CH_3$ | $CH_3$ | H | $n\text{-}C_3H_7$ |
| 25 | $CH_3$ | H | $CH_3$ | $CH_3$ | H | $CH(C_2H_5)_2$ |
| 26 | $CH_3$ | H | $CH_3$ | $CH_3$ | H | $n\text{-}C_6H_{13}$ |
| 27 | $CH_3$ | H | $CH_3$ | $CH_3$ | $CH_3$ | $CH_3$ |
| 28 | $CH_3$ | H | $CH_3$ | $CH_3$ | H | Phenyl |
| 29 | $CH_3$ | H | $CH_3$ | $CH_3$ | H | Furyl |

EXAMPLE 30

2-Furyl-4,4,6-trimethyl-3,4,5,6-tetrahydropyrimidine

In a 1 pt. pressure reactor was placed 196 g. of mesityl oxide and 192 g. of furfural. To the mixture was added over a 3 hr. period 68 g. of ammonia gas. After the addition was completed, the mixture was stirred for 17 hrs. The water produced was removed under diminished pressure to yield 374 g. of 2-furyl-4,4,6-trimethyl-2,3,4,5-tetrahydropyrimidine, infrared spectrum, 3.08μ, NH; 6.00μ, C=N; $b_{2.5}$ 89°–91° C.; nuclear magnetic resonance spectrum, solvent $CDCl_3$, δ in ppm. 7.40 m, 1H; 6.33 m, 2H; 5.50 m, 1H; 1.98 2 s's, 5H; 1.16 & 1.12 2 s's, 6H.

Anal. Calc.ed for $C_{11}H_{16}N_2O$; N, 14.54 Found; N, 14.38

A sample of 150 g. of 2-furyl-4,4,6-trimethyl-2,3,4,5-tetrahydropyrimidine and 10 g. of solid sodium hydroxide were heated to 180° C. over a 2 hr. period. The resulting product was distilled under diminished pressure to yield 52 grams of 2-furyl-4,4,6-trimethyl-3,4,5,6-tetrahydropyrimidine $b_{2.0}$ 120°–122° C., solidified during distillation; infrared spectrum, 3.06μ, NH, 6.20μ, C=N. Nuclear magnetic resonance spectrum, solvent $CDCl_3$; δ in ppm. 7.38 m, 1H; 6.90 m, 1H; 6.40 m, 1H; 3.55 m, 1H; 1.72 d of d's, 2H; 1.25 d, 3H; 1.20 s, 6H.

Anal. Calc.ed for $C_{11}H_{16}N_2O$; N, 14.59 Found; N, 14.40

In a manner as described in example 30, the following substituted 3,4,5,6-tetrahydropyrimidines summarized in Table III were prepared from the corresponding 2,3,4,5-tetrahydropyrimidines.

Table III

| Ex. No. | $R_1$ | $R_2$ | $R_3$ | $R_4$ | $R_5$ | $R_6$ |
|---|---|---|---|---|---|---|
| 31 | $CH_3$ | H | $CH_3$ | $CH_3$ | H | Phenyl |
| 32 | $CH_3$ | H | $CH_3$ | $CH_3$ | H | 2'-Pyridyl |
| 33 | $CH_3$ | H | $CH_3$ | $CH_3$ | H | 4'-Pyridyl |
| 34 | $CH_3$ | H | $CH_3$ | $CH_3$ | $CH_3$ | Phenyl |
| 35 | $CH_3$ | H | $CH_3$ | $CH_3$ | $CH_3$ | 4'-methoxyphenyl |

The compositions of this invention are useful as corrosion inhibitors, biocides, fuel additives, fuel antifoulants, scale inhibitors, antistatic agents, chelating agents, etc.

It will be apparent that various changes and modifications may be made in the invention described herein, without departing from the scope of the invention. It is intended, therefore, that all matter contained herein shall be interpreted as illustrative only and not as limitative.

USE AS CORROSION INHIBITORS

The compounds of this invention are particularly useful as corrosion inhibitors, particularly in acidic systems.

USE IN FLUIDS FOR DRILLING WELLS

This phase of the invention relates to the use of the compounds of this invention as corrosion inhibitors in producing an improved drilling fluid useful in drilling oil and gas wells.

Fluids commonly used for the drilling of oil and gas wells are of two general types: water-base drilling fluids comprising, for example, a clay suspended in water, and oilbase drilling fluids comprising, for example, a clay or calcium carbonate suspended in mineral oil.

A third type of drilling fluid which has recently been developed, is one of oil-in-water or water-in-oil emulsion, for example, emulsions of mineral oil in water or water in mineral oil formed by means of emulsifiers such as fulfuric acid; Turkey-red oil; soaps of fatty acids, for example, sodium oleate; emulsoid colloids, for example, starch, sodium alginate, etc. Varying amounts of finely divided clay, silica, calcium carbonate, blown asphalt and other materials may be added to these emulsions to improve their properties and control their weight.

I have now discovered that the compositions of this invention can be employed as a corrosion inhibitor in drilling fluids.

USE IN AIR DRILLING

It has long been conventional practice in drilling deep bore holes to circulate a drilling mud down through the drill stem and up through the bore hole between the wall of the bore hole and the drill stem for the removal of chips or cuttings from the bore hole and to provide support for the wall of the bore hole. More recently, in the drilling of holes in which wall support provided by drilling mud is not employed, drilling has been carried out with the use of air for chip removal. Such drilling is not only normally faster than mud drilling but is indispensable in areas where the supply of water is limited or when drilling through cavernous formations into which the drilling mud flows and becomes lost.

The increasing popularity of air or gas drilling has come about not only because this method of drilling is frequently faster, as noted above, but for the additional reasons that the drill bits last longer, the provision and handling of water under wide ranges of temperature conditions is avoided, boring samples are easily observed when they are not mixed with mud, and there is no loss involved as in the case of mud drilling when drilling through cavernous formations. Furthermore, prompt removal of water entering the hole maintains a dry hole and the likelihood of wall collapse is thereby reduced.

In a typical air drilling operation there may be provided, for example, an up-flow of air in the bore hole having a velocity of the order of 3,000 feet per minute. This flow of air upwardly through the bore hole, which is produced by air pumped downwardly through the drill stem, provides adequate removal of cuttings. The air is delivered to the drill stem at pressures of 20 to 60 lbs. per square inch and for dewatering or for breaking obstructions, as will be hereinafter described, the pressures may be increased to 180 to 200 lbs. or more per square inch.

Air drilling operations are frequently hampered by the inflow of water into the bore hole when the drill bit is penetrating a water bearing stratum or when the bore hole has passed through a water bearing stratum that has not been cased. Normally, if drilling proceeds uninterruptedly both before and during penetration into a water bearing stratum, the flow of air is sufficient to blow the water out of the bore hole along with the cuttings and drilling dirt. There are, however, two major problems encountered in air drilling when water is entering the bore hole. The first problem occurs when there is a small inflow of water sufficient to cause a dampening of the cuttings which, under certain conditions, will then ball-up, clogging and sometimes jamming the drill bit. The second problem is encountered when there is a substantial amount of water remaining in the bottom of the bore hole during drilling causing a sloughing of the side wall of the bore hole. This latter condition may arise even though the water entering the bore hole is being blown out of the hole as fast as it enters. If there is a substantial inflow of water or if there is a substantial flow of water past a region of the bore hole susceptible to this condition, the water passing that region of the bore hole may cause a sloughing of the side wall.

The addition of foam forming materials to the air flow when air drilling is employed in conjunction with sufficient water to provide foaming gives rise to numerous advantages in drilling operations. The water may be introduced either through a water bearing stratum being penetrated by the drill bit or, alternatively, if the hole is dry, water may be introduced from the surface of the earth through the drill stem in conjunction with the delivery of compressed air and foam forming material through the drill stem to the drill bit. In either case the water may be said to be existing in the bore hole, and drilling operations are described in U.S. Pat. No. 3,130,798.

The amount of the compositions of the invention to be employed as a corrosion inhibitor can vary widely depending upon particular compounds, the particular system, the amounts of oxygen present, etc. I may employ concentrations of from about 0.5 to 5,000 ppm, such as from about 4 to 4,000 ppm, for example from about 20 to 2,000 ppm, but preferably from about 100 to 1,000 ppm. The optimum amount, to be determined in each instance, which will depend on function and economics, can be lesser or greater than the above amounts under proper conditions.

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantities of oil can no longer be obtained by the usual pumping methods, various processes are sometimes used for the treatment of the oil-bearing formation in order to increase the flow of the oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals.

I have now discovered a method of preventing corrosion in systems containing a corrosive aqueous media, and most particularly in systems containing brines, which is characterized by employing the compositions of this invention.

I have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances, therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the compound of this invention, sufficient to prevent corrosion, in concentrations of about 10 ppm to 10,000 ppm, or more, for example, about 50 to 5,000 ppm, but preferably about 15 to 1,500 ppm. The upper limiting amount of the compounds is determined by economic considerations. Since the success of a water flooding operation manifestly depends upon its total cost being less than the value of the additional oil recovered from the oil reservoir, it is quite important to use as little as possible of these compounds consistent with optimum corrosion inhibition. Optimum performance is generally obtained employing about 1,000 ppm. Since these compounds are themselves inexpensive and are used in low concentrations, they enhance the success of a flood operation by lowering the cost thereof.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example, five spot flooding, peripheral flooding, etc., and in conjunction with other secondary recovery methods.

Corrosion tests were made using sand blasted 1020 mild steel coupons monitored by a polarization resistance meter, a Pair instrument described in U.S. Pat. No. 3,406,101. These tests were made in beakers of 1,500 cc volume with provision for constant stirring, an air inlet kept the fluids constantly saturated with air. Results of these corrosion tests made in the aqueous environment are shown in the Table.

Protection is calculated in the usual manner from corrosion rate ($R_1$) of fluids without inhibitor and corrosion rate ($R_2$) in presence of particular inhibitor according to the formula $(R_1-R_2)/(R_1) \times 100$ = percent protection.

The following aerated brine was employed in the tests: 4.2% NaCl, 1.7% $MgCl_2$, 0.15% $CaCl_2$, 0.09% $Na_2SO_4$, pH 6.0.

Table IV

Corrosion tests at ambient temperature in continuously aerated brine, corrosion rate in mpg.

Blank rate = 95 mpg, inhibitor concentration 1,000 ppm.

| Product of Example No. | Time in Hours | Corrosion Rate mpg | % Protection |
|---|---|---|---|
| 1 | 24 | 66 | 30 |
| 7 | 2 | 58 | 39 |
| 7 | 24 | 56 | 41 |
| 9 | 24 | 50 | 47 |
| 16 | 24 | 24 | 72 |
| 17 | 24 | 28 | 70 |
| 35 | 2 | 21 | 78 |
| 35 | 24 | 18 | 81 |

I claim

1. A process of converting 2,3,4,5-tetrahydropyrimidines (Δ-1) having at least one hydrogen in the 2-position to 3,4,5,6-tetrahydropyrimidines (Δ-2) which comprises the steps of hydrogenating and dehydrogenating said Δ-1 compounds in the presence of a hydrogenation-dehydrogenation catalyst.

2. The process of claim 1 where hydrogenating and dehydrogenating is done in two steps.

3. The process of claim 1 where hydrogenating and dehydrogenating is done in one step.

4. A process of converting hexahydropyrimidines having at least one hydrogen in the 2-position to 3,4,5,6-tetrahydropyrimidines (Δ-2) which comprises the step of dehydrogenating said hexahydropyrimidines in the presence of a dehydrogenation catalyst.

5. A process of converting 2,3,4,5-tetrahydropyrimidines (Δ-1) having one hydrogen in the 2-position and an aromatic radical in the 2-position to the corresponding 3,4,5,6-tetrahydropyrimidines (Δ-2) which comprises heating said Δ-1 compound in the absence of a solvent or under basic conditions so as to form the Δ-2 compound.

6. The process of claim 5 which is carried out in the absence of a solvent.

7. The process of claim 5 which is carried out under basic conditions.

8. The process of claim 5 where the base is sodium hydroxide or potassium hydroxide.

9. The process of claim 5 where the aromatic radical is phenyl, methoxyphenyl, furyl or pyridyl.

* * * * *